(12) United States Patent
Majumdar et al.

(10) Patent No.: US 10,399,044 B2
(45) Date of Patent: Sep. 3, 2019

(54) THIN FILM COMPOSITE MEMBRANES FOR SEPARATION OF ALKENES FROM ALKANES

(71) Applicant: COMPACT MEMBRANE SYSTEMS, INC., Newport, DE (US)

(72) Inventors: Sudipto Majumdar, Newark, DE (US); Andrew Edward Feiring, Wilmington, DE (US); Ning Shangguan, Cherry Hill, NJ (US); Yosuke Koizumi, Bear, DE (US)

(73) Assignee: COMPACT MEMBRANE SYSTEMS, INC., Newark, DE (US)

( * ) Notice: Subject to any disclaimer, the term of this patent is extended or adjusted under 35 U.S.C. 154(b) by 84 days.

(21) Appl. No.: 15/573,442

(22) PCT Filed: May 6, 2016

(86) PCT No.: PCT/US2016/031135
§ 371 (c)(1),
(2) Date: Nov. 10, 2017

(87) PCT Pub. No.: WO2016/182887
PCT Pub. Date: Nov. 17, 2016

(65) Prior Publication Data
US 2018/0111098 A1    Apr. 26, 2018

Related U.S. Application Data

(60) Provisional application No. 62/262,169, filed on Dec. 2, 2015, provisional application No. 62/159,668, filed on May 11, 2015, provisional application No. 62/159,646, filed on May 11, 2015.

(51) Int. Cl.

| | | |
|---|---|---|
| *B32B 3/26* | (2006.01) |
| *C08F 4/34* | (2006.01) |
| *B01D 53/22* | (2006.01) |
| *B01D 69/02* | (2006.01) |
| *B01D 69/12* | (2006.01) |
| *B01D 71/26* | (2006.01) |
| *B01D 71/32* | (2006.01) |
| *B01D 71/34* | (2006.01) |
| *B01D 71/76* | (2006.01) |
| *B01D 71/82* | (2006.01) |
| *B32B 27/08* | (2006.01) |
| *B32B 27/20* | (2006.01) |
| *B32B 27/28* | (2006.01) |
| *B32B 27/32* | (2006.01) |
| *C07C 7/144* | (2006.01) |
| *C08G 61/10* | (2006.01) |
| *C08F 214/20* | (2006.01) |
| *C08F 214/26* | (2006.01) |
| *C08F 216/14* | (2006.01) |

(52) U.S. Cl.
CPC .......... *B01D 71/76* (2013.01); *B01D 53/228* (2013.01); *B01D 69/02* (2013.01); *B01D 69/12* (2013.01); *B01D 71/26* (2013.01); *B01D 71/32* (2013.01); *B01D 71/34* (2013.01); *B01D 71/82* (2013.01); *B32B 3/26* (2013.01); *B32B 27/08* (2013.01); *B32B 27/205* (2013.01); *B32B 27/28* (2013.01); *B32B 27/286* (2013.01); *B32B 27/322* (2013.01); *C07C 7/144* (2013.01); *C08F 4/34* (2013.01); *C08F 214/202* (2013.01); *C08F 214/262* (2013.01); *C08F 216/1408* (2013.01); *C08F 216/1466* (2013.01); *C08G 61/10* (2013.01); *B01D 2325/20* (2013.01); *B32B 2307/70* (2013.01); *B32B 2307/724* (2013.01); *B32B 2307/732* (2013.01); *C08F 2216/1475* (2013.01)

(58) Field of Classification Search
None
See application file for complete search history.

(56) References Cited

U.S. PATENT DOCUMENTS

| | | | |
|---|---|---|---|
| 3,758,603 A | 9/1973 | Steigelmann et al. | |
| 3,758,605 A | 9/1973 | Hughes et al. | |
| 4,614,524 A | 9/1986 | Kraus | |
| 4,731,263 A | 3/1988 | Martin et al. | |
| 4,741,744 A * | 5/1988 | Wu | B01D 67/0093 95/47 |
| 5,015,268 A | 5/1991 | Ho | |
| 5,051,114 A | 9/1991 | Nemser et al. | |
| 5,062,866 A | 11/1991 | Ho | |
| 5,191,151 A | 3/1993 | Eriksen et al. | |
| 5,670,561 A | 9/1997 | Pinnau et al. | |
| 5,914,154 A | 6/1999 | Nemser | |
| 6,361,582 B1 | 3/2002 | Pinnau et al. | |
| 6,468,331 B2 | 10/2002 | Kang et al. | |

(Continued)

OTHER PUBLICATIONS

European Extended Search Report of European Application No. EP16793240.9 dated Nov. 15, 2018, 5 pages.

(Continued)

*Primary Examiner* — Krishnan S Menon
(74) *Attorney, Agent, or Firm* — Devlin Law Firm LLC; James M. Lennon

(57) ABSTRACT

Composite membranes comprised of at least two layers, one of the layers being a silver ionomer and a second layer which is a fluorinated polymer with certain permeability properties, are especially useful for the separation of alkanes from alkenes, Particularly useful is a three-layer composite membrane in which a porous layer is laminated to the second layer.

50 Claims, No Drawings

(56) References Cited

U.S. PATENT DOCUMENTS

| | | |
|---|---|---|
| 6,518,476 B1 | 2/2003 | Culp et al. |
| 6,706,771 B2 | 3/2004 | Kim et al. |
| 6,878,409 B2 | 4/2005 | Kim et al. |
| 7,179,321 B2 | 2/2007 | Kang et al. |
| 7,220,508 B2 | 5/2007 | Watalabe et al. |
| 7,361,800 B2 | 4/2008 | Hererra et al. |
| 7,491,262 B2 | 2/2009 | Kang et al. |
| 2001/0025819 A1 | 10/2001 | Bowser |
| 2003/0008990 A1 | 1/2003 | McCarthy |
| 2003/0023015 A1 | 1/2003 | Tatemoto et al. |
| 2003/0033929 A1 | 2/2003 | Pinnau et al. |
| 2003/0104150 A1 | 6/2003 | Bonnet et al. |
| 2004/0102591 A1 | 5/2004 | Brookhart et al. |
| 2004/0167289 A1 | 8/2004 | Beriarian et al. |
| 2004/0173529 A1 | 9/2004 | Da Costa et al. |
| 2005/0009944 A1 | 1/2005 | Apostolo et al. |
| 2006/0014887 A1 | 1/2006 | Hamrock et al. |
| 2007/0066691 A1* | 3/2007 | Arcella ............ B01D 67/0013 521/27 |
| 2007/0088142 A1 | 4/2007 | Ikeda et al. |
| 2011/0266220 A1 | 11/2011 | Campos et al. |
| 2012/0097612 A1 | 4/2012 | Nemser et al. |
| 2015/0025293 A1 | 1/2015 | Feiring et al. |
| 2015/0119577 A1 | 4/2015 | Campos et al. |

OTHER PUBLICATIONS

Maat et al., "The removal of hydrogen sulfide from gas streams using an aqueous metal sulfate A absorbent: Part 1. The absorption of hydrogen sulfide in metal sulfate solution" Separation and 1-11,13-14 Purification Technology, vol. 43, No. 3, pp. 183-197 (2005) entire document, especially p. 183-184.

European Extended Search Report of European Application No. EP16793238.3 dated Nov. 9, 2018, 5 pages.

* cited by examiner

THIN FILM COMPOSITE MEMBRANES FOR SEPARATION OF ALKENES FROM ALKANES

CROSS-REFERENCE TO RELATED APPLICATIONS

This application is a National Stage Entry of International Patent Application No. PCT/US2016/031335, filed May 6, 2016, which claims the benefit of priority to U.S. Provisional Patent Application No. 62/262,169, filed Dec. 2, 2015, U.S. Provisional Patent Application No. 62/159,646, filed May 11, 2015, and U.S. Provisional Patent Application No. 62/159,668, filed May 11, 2015, the disclosures of which are incorporated by reference herein in their entirety.

GOVERNMENT RIGHTS

Support was provided under Department of Energy awards of DE-SC0004672 and DE-SC0007510. The U.S. government has rights in this patent application.

FIELD OF THE INVENTION

Thin film composite membranes which have one or more layers of a certain type of silver ionomer, and which can separate alkanes from alkenes, are described.

TECHNICAL BACKGROUND

Membranes containing layers of silver ionomers of certain sulfonic acid containing polymers, especially fluorinated polymers, have been used to separate alkanes from alkenes. The separation of these types of compounds, especially those having the same number of carbon atoms, such as ethylene from ethane, propylene from propane, and pentene from pentane are often difficult by other methods, because for instance the boiling points of the alkane and alkene are similar, resulting in high energy requirements. This is especially true for lower boiling materials containing 2 to four carbon atoms, which would require cryogenic distillation, usually very energy intensive.

In membrane separation processes, thin film composite membranes are often used. Thin-film composite membranes (TFCs) usually consist of layers of dissimilar materials joined together to form a single membrane. This layered construction permits use of material combinations that optimize the performance and durability of the membrane. The same is true of alkane-alkene separation processes using silver ionomers, described herein are new TFCs for such separations.

As a minimum requirement one might believe that a membrane having a single layer, a "separation layer" (SL), of silver ionomer would be useful. However, such a type of membrane has two important drawbacks, the silver ionomer is expensive, and in thicker membranes which are required for the membrane to have sufficient strength, the permeance to the alkene, the amount of alkene which can pass through the membrane per unit time is relatively low. Therefore one (or more) thin separation layers are required for practical membranes. A composite membrane with another layer of material which physically supports the entire TFC, and which is laminarly contacting the separation layer can be added. This other layer is nonporous and the material passing through the TFC (in this case one or more alkenes), should also preferably diffuse through this other layer rapidly. Herein this other layer is called the high diffusion rate layer (HDR).

The use of various composite membranes with silver ionomer separation layers for the separation of alkanes from alkenes is known, see for instance A. van Zyl, et al., *Journal of Membrane Science*, 133, (1997), pp. 15-26, O. I. Eriksen, et al., *Journal of Membrane Science*, 85 (1993), pp. 89-97, and A. J. van Zyl, *Journal of Membrane Science*, 137 (1997), pp. 175-185, and U.S. Pat. No. 5,191,151. However none of these references describe a TFC in which a separation layer of a silver ionomer is used in combination an HDR layer described herein.

Certain layers in TFCs, layers, sometimes termed "gutter layers" are used, and are generally described in M. Kattula, et al., *Designing ultrathin film composite membranes: the impact of a gutter layer, Scientific Reports*, 5, Article Number 15016 (2015). There is no specific information concerning alkane-alkene separations using silver ionomers.

SUMMARY OF THE INVENTION

This invention concerns, a thin film composite membrane for the separation of alkanes from alkenes, comprising:

(a) a separation layer comprising a silver ionomer of a polymeric sulfonic acid; and (b) a high diffusion rate layer of a fluorinated polymer having a permeance to nitrogen of at least about 250 GPU wherein said separation layer and said high diffusion rate layer are laminated to each other.

DETAILS OF THE INVENTION

Herein certain terms are used and some of them are defined below.

What is meant by a fluorinated polymer or ionomer is of the total of the carbon-hydrogen groups and the carbon fluorine groups in the ionomer, about 20% or more are carbon-fluorine groups, preferably about 50% or more, very preferably about 70% or more, especially preferably about 90% or more, and very especially preferably about 95% or more are carbon fluorine groups, or most preferably are perfluoropolymers. By a carbon-hydrogen group is meant a hydrogen atom bound directly to a carbon atom, while a carbon-fluorine group is a fluorine atom bound directly to a carbon atom. Thus —$CF_2$— groups contains 2 carbon fluorine groups, while a —$CH_3$ group contains 3 carbon-hydrogen groups. Thus in a homopolymer of vinylidene fluoride, in which the repeat groups are —$CH_2CF_2$-the carbon-hydrogen groups and the carbon fluorine groups are each 50% of the total of carbon-hydrogen plus carbon-fluorine groups present. In a copolymer of 50 mole percent perfluoro(2,2-dimethyl-1,3-dioxole) and 50 mole percent ethylene the carbon-hydrogen groups are 33.3% of the total of the carbon-fluorine plus carbon hydrogen groups present, and the carbon-fluorine groups are 66.7% of the carbon-fluorine and carbon-hydrogen groups present. The relative amount of carbon-fluorine and carbon hydrogen groups present can be determined by elemental analysis, NMR spectroscopy, for instance using $^{14}C$ NMR, or a combination of any of these.

By a "driving force" in the separation of the alkene and alkane in the gaseous state is generally meant that the partial pressure of alkene on the first ("feed") side of the membrane is higher than the partial pressure of alkene on the second ("product") side of the membrane. For instance this may be accomplished by several methods or a combination thereof.

One is pressurizing first side to increase the partial pressure of alkene on the first side, second is sweeping the second side by inert gas such as nitrogen to lower the partial pressure of the alkene on the second side, and third is reducing pressure of second side by vacuum pump to lower the partial pressure of the alkene on the second side. These and other known methods in the art of applying a driving force may be used.

This may be quantified for a separation of gases to some extent by a mathematical relationship:

$$Q_a \alpha F_a(P1_a - P2_a)$$

wherein $Q_a$ is the flow rate of component "a" through the membrane, $F_a$ is the permeance of component a through the membrane, $P1_a$ is the partial pressure on the first (feed) side, and $P2_a$ is the partial pressure on the second (product) side.

By "laminated" is meant the two layers concerned are in intimate contact with each other. This is often referred to as "bonded together" although usually no separate adhesive is employed.

Preferably the SL is about 0.1 μm to about 1.0 μm thick, more preferably about 0.2 μm to about 0.5 μm thick. As mentioned above the relative thinness of this layer help to improve the productivity of the overall separation process per unit area of membrane.

Polymers useful for the SL are silver ionomers of sulfonic acid containing polymers. Such ionomers are well known in the art, and in some instances known to separate alkanes from alkenes, see for instance U.S. patent application Ser. No. 14/334,605, U.S. Provisional Application Ser. Nos. 62/159,646, 62/159,668, and 62/262,169 (now PCT application Nos. PCT/US2016/031117, PCT/US2016/031122, PCT/US2016/031130, PCT/US2016/031135, and PCT/US2016/031140, respectively), A. van Zyl, et al., *Journal of Membrane Science*, 133, (1997), pp. 15-26, 0.1. Eriksen, et al., *Journal of Membrane Science*, 85 (1993), pp. 89-97, and A.J. van Zyl, *Journal of Membrane Science*, 137 (1997), pp. 175-185, and U.S. Pat. No. 5,191,151, all of which are hereby included by reference. A preferred grade of Teflon® AF is AF 2400, which is reported to contain 83 mole percent PDD, and 17 mole percent tetrafluoroethylene. Polymers of PDD with other comonomers, such as perfluoro(propylvinyl ether) and $CF_2$=$CFOCF_2CF(CF_3)OCF_2CF_2SO_2F$, may also be employed. In copolymers of PDD with these alternative monomers, it is preferred that the PDD content be at least 90 mole percent.

The sulfonic acid containing polymers that form the silver ionomers in the SL, and of course the ionomers themselves, are preferably fluorinated polymers, and more preferably 50% or more, very preferably 70% or more, and truly preferably 90% or more are carbon fluorine groups. Especially preferably this polymer is a perfluoropolymer, that is all the monomer being polymerized to repeat unit contain no hydrogen. Such perfluoropolymers may have very small amounts of "adventitious" carbon hydrogen groups from impure monomers, or groups such as initiator fragments bonded to chains.

In the fluorinated polymers in the HDL, and preferably 50% or more, more preferably 70% or more, and very preferably 90% or more are carbon fluorine groups. Especially preferably this polymer is a perfluorinated polymer, that is all the monomer being polymerized to repeat unit contain no hydrogen. Such perfluoropolymers may have very small amounts of "adventitious" carbon hydrogen groups from impure monomers, or groups such as initiator fragments bonded to chains.

Preferably the HDL layer is about 0.05 μm to about 0.5 μm thick, more preferably about 0.05 μm to about 0.2 μm thick.

Particularly preferred polymers for the HDL are copolymers of perfluoro(2,2-methyl-1,3-dioxole), (PDD) particularly if included in a perfluoropolymer. In any copolymer of the PDD it is preferred that at least about 50 mole percent of the total repeat units are derived from PDD, more preferably at least 80 mole percent. Generally speaking higher molar percentages of PDD are desired in all PDD copolymers, consistent with being able to process the polymers into a layer in the membrane. A preferred copolymer is that of PDD with tetrafluoroethylene, available as Teflon® AF (The Chemours Co., Wilmington, Del. 19899, USA) and for further information about Teflon® AF, see P. R. Resnick, et al., *Teflon AF Amorphous Fluoropolymers*, J. Schiers, Ed., *Modem Fluoropolymers*, John Wiley & Sons, New York, 1997, p. 397-420, which is hereby included by reference. A preferred grade of Teflon® AF is AF 2400, which is reported to contain 83 mole percent PDD, and 17 mole percent tetrafluoroethylene.

Other potentially useful polymer in the HDL include Cytop® fluoropolymer resin (reportedly a homopolymer f 1,1,2,4,4,5,5,6,7,7-decafluoro-3-oxa-1-,6-heptadiene) available from Asahi Glass, 1-5-1, Marunouchi, Chiyoda-ku, Tokyo 100-8405, Japan, and Hyflon® DA-type fluoropolymer resin, (reportedly a copolymer of tetrafluoroethylene and perfluoro(3-methoxy-1,3-dioxole) available from Solvay, SA, RUE DE RANSBEEK, 310, 1120 Bruxelles, Belgium.

Preferably the polymer(s) in of the HDL are so-called "glassy" polymers. By that is meant the polymer has no melting point above about 30° C. with a heat of fusion of 3 J/g or more when measured by Differential Scanning calorimetry using ASTM Test D3418-12e1 using a heating and cooling rate of 10° C./min, and measured on the second heat. Also a glassy polymer has a Glass Transition Temperature (Tg) above about 40° C., more preferably about 40° C. The Tg is measured according to ASTM Test D3418-12e1 at a heating and cooling rate of 10° C./min, and the Tg is taken as the midpoint (inflection point) of the transition on the second heat. Preferably the Tg is less than about 220° C., because for instance if the Tg is too high it may be difficult to dissolve the polymer to form a coating or layer.

The polymers for the HDL may contain functional groups but preferably these functional groups are relatively difficult to oxidize and will not complex or react with the silver ion in the SL. Useful groups include perfluoroether and choro (particularly when present as chlorotrifluoroethylene). Groups which preferably are not present are primary and secondary alcohol. Iodo, bromo, and aldehyde.

The HDL has a permanence to nitrogen of at least 250 GPU at about 25° C. Preferably this permanence should be at least about 500 GPU and more preferably at least about 1000 GPU, especially preferably about 1500 GPU, and very preferably at least about 2500 GPU, and most preferably at least about 5000 GPU. If the permanence to alkenes is high enough a relatively thick layer of the HDL material may be used, and this would support a membrane having only two layers, the HDL and SL.

However such nonporous very highly permeable materials are difficult to find and so in many instances a third layer is added a (micro)porous layer, a layer containing many small pores through which the desired may flow relatively unobstructed, while the HDL is very thin so that the productivity of the TFC is high per unit area. This porous layer (PL) may be made thick enough to physically support the entire three (or more) layer TLC without sacrificing much productivity.

When these three types of layers, the SL, HDL and PL are combined into a single TLC, the structure of the TLC, in order of layers, is typically SL/HDL/PL (the slashes indicating where layer surfaces are laminated together), with the SL being exposed to the mixture from which one or more components is to be separated, and the separated product passing through the HDL and emerging from the "free surface" of the PL or vice versa In this type of configuration, the HDL is often termed the "gutter layer". It is known that this gutter layer often improves the throughput of the TLC per unit area of TLC, see M. Kattula, et al., *Designing ultrathin film composite membranes: the impact of a gutter layer, Scientific Reports,* 5, Article Number 15016 (2015), which is hereby included by reference.

In the present invention however the gutter layer has another unexpected effect, improving the separation of the TLC as a whole. Not wishing to be bound by theory, generally speaking materials (usually polymers) chosen for the various layers of a TLC are chosen partially because under the conditions the TLC will be used they are chemically and physically stable. Unfortunately the silver ionomers of the SL layer are not very chemically stable, especially in the presence of organic compounds which can be relatively readily oxidized. Most materials for the PLs, organic polymers which often contain small amounts of adventitious chemical materials or oxidizable groups in the polymers themselves, which are oxidized by $Ag^+$, the silver often being reduced the metal, and thereby becoming ineffective in separating alkanes from alkenes.

This is why it is believed that the fluoropolymers, especially perfluoropolymers, described herein for the HDL are effective in not only perhaps improving productivity of the membrane, but in the proper configuration help protect the integrity of the SL, improving its "separation properties" initially and over a longer period of time, see for instance Table 1 below.

Other layers and layer configurations may be present in the HDL. For instance an additional HDL layer may be present, preferably in the HDL/SL/HDL/PL configuration wherein the additional HDL layer protects the "exposed" surface of the three layer HDL with a SL/HDL/PL from contamination and perhaps degradation from materials in the mixture which is to be (partially) separated. Other useful layers and configurations will be apparent to those skilled in the art.

The use of these types of membranes which have one or more dense silver ionomer layers to separate alkanes from alkenes is well known in the art. One side of the membrane is exposed to a gaseous or liquid mixture of one or more alkanes and one or more olefins and a driving force is provided. An eluate stream comes out of the other side of the membrane which is enriched on alkene(s), that is the concentration of the alkane(s) in the alkene(s) is reduced. It is preferred if the mixture of alkane(s) and alkene(s) is gaseous. Such separation process are described in U.S. patent application Ser. No. 14/334,605, and U.S. Provisional Application Ser. Nos. 62/159,646, 62/159,668, and 62/262,169 (now PCT application Nos. PCT/US2016/031117, PCT/US2016/031122, PCT/US2016/031130, PCT/US2016/031135, and PCT/US2016/031140, respectively), A. van Zyl, et al., *Journal of Membrane Science,* 133, (1997), pp. 15-26, O. I. Eriksen, et al., *Journal of Membrane Science,* 85 (1993), pp. 89-97, and A. J. van Zyl, *Journal of Membrane Science,* 137 (1997), pp. 175-185, and U.S. Pat. No. 5,191,151, all of which are hereby included by reference.

The HDL must have a minimum permeance to nitrogen at about 25° C. of at least about 500 GPU, preferably at least about 1000 GPU, more preferably at least about 1500 GPU and very preferably at least about 2000. To obtain high permeances for such layers, these layers are typically made out of polymers which have a high permeability to the gas being tested, in this instance nitrogen, and are generally quite thin, because the higher the thickness the lower the permeance. Thus these SLs can be about 0.1 to about 1.0 µm thick, preferably about 0.2 to about 0.5 µm thick. It may be difficult to measure permeances on layer by themselves that are so thin because of damage from forming and handling such thin layers. Thus the measurement of the permeance of the HDL can be measured with the HDL supported by a porous layer, the porous layer having a much higher "permeance" to the gas being tested than the HDL itself. If possible a membrane having HDL layer, and for instance the porous layer, are both made by the same process used to make the actual membrane which is to be used to the olefin/alkane separation, see for instance the preparation of the as "Teflon AF/PAN" substrate in Example 3 below.

One can search for potential polymers useful in SDLs by finding the permeabilities to nitrogen of various otherwise suitable polymers. GPU units herein have the units of $(1 \times 10^{-6})$ sec/cm$^2$·s·cm Hg, while permeability units are often in Barrer, which are $(1 \times 10^{-10})$ sec·cm/cm$^2$·s·cm H.

Method of Measuring Nitrogen Permeance of the HDL

A 47 mm flat disc membrane containing only gutter layer material as a membrane on a porous support is punched from a larger 3 inch flat sheet membrane. The 47 mm disc is then placed in a stainless steel cross flow testing cell comprised of a feed port, retentate port, a sweep inlet port, and a permeate port. Four hex bolts are used to tightly secure the membrane in the testing cell with a total active area of 13.85 cm$^2$.

The feed port of the cell is connected to a gas manifold consisting of 4 gases: nitrogen, oxygen, helium, and carbon dioxide. The retentate port is connected to a ball valve to dead end the gas flow as well as the purge the gas. One of the two permeate ports is shut and the other is connected to a flow meter.

Nitrogen is brought up to pressure by a gas regulator and allowed to purge slowly for 1 minute. The retentate port is closed and a flow measurement can be taken from the permeate which is at atmospheric pressure. This process is repeated for three different feed pressures between 5 to 10 psig so that an average permeance can be calculated. The feed pressure, permeate flowrate, and temperature are recorded for the calculation. The permeance can be calculated by the equation:

$$Q = F/(A \cdot \Delta p)$$

where, Q=gas permeance, F=permeate flow rate, $\Delta P$=transmembrane pressure difference, and A is the effective area of the membrane, in this instance 13.85 cm$^2$.

Determination of Permeance and Selectivity for Olefin/Alkane Separations

For determinations of permeance (GPU, reported in units of sec/cm$^2$·s·cm Hg) and selectivity the following procedure was used. A 47 mm flat disc membrane was punched from a larger flat sheet 3 inch composite membrane. The 47 mm disc is then placed in a stainless steel cross flow testing cell comprised of a feed port, retentate port, a sweep inlet port, and a permeate port. Four hex bolts were used to tightly secure the membrane in the testing cell with a total active area of 13.85 cm$^2$.

The cell was placed in a testing apparatus comprising of a feed line, a retentate line, a sweep line, and a permeate line. The feed consisted of a mixture of an olefin (propylene) gas and a paraffin (propane) gas. Each gas was supplied from a separate cylinder. For olefin, polymer grade propylene (99.5 vol % purity) was used and for paraffin, 99.9 vol % purity propane was used. The two gases were then fed to their respective mass flow controllers where a mixture of any composition can be made. The standard mixing composition was 20 vol % olefin and 80 mol % paraffin at a total gas flow rate of 200 mL/min. The mixed gas was fed through a water bubbler to humidify the gas mixture bringing the relative humidity to greater than 90%. A back pressure regulator is used in the retentate line to control the feed pressure to the membrane. The feed pressure was normally kept at 60 psig (0.41 MPa) after the back pressure regulator the gas is vented.

The sweep line consisted of a pure humidified nitrogen stream. Nitrogen from a cylinder was connected to a mass flow controller. The mass flow controller was set to a flow of 300 mL/min. The nitrogen was fed to a water bubbler to bring the relative humidity to greater than 90%. After the bubbler the nitrogen was fed to the sweep port of the membrane to carry any permeating gas through to the permeate port.

The permeate line consisted of the permeated gas through the membrane and the sweep gas as well as water vapor. The permeate was connected to a three way valve so flow measurements could be taken. A Varian® 450 GC gas chromatograph (GC) with a GS-GasPro capillary column (0.32 mm, 30 m) was used to analyze the ratio of the olefin and paraffin in the permeate stream. The pressure in the permeate side was typically between 1.20 and 1.70 psig (8.3 to 11.7 kPa), but for Examples herein was 0.0 to 0.3 psig ("0" to 2.1 kPa). Experiments were carried out at room temperature.

During experiment the following were recorded: feed pressure, permeate pressure, temperature, sweep-in flow rate (nitrogen+water vapor) and total permeate flow rate (permeate+nitrogen+water vapor).

From the results recorded the following were determined: all individual feed partial pressures based on feed flows and feed pressure; all individual permeate flows based on measured permeate flow, sweep flows, and composition from the GC; all individual permeate partial pressures based on permeate flows and permeate pressures.

From these the transmembrane partial pressure difference of individual component were calculated. From the equation for permeance $$Q_i = F_i / (A \cdot \Delta p_i)$$

wherein, $Q_i$=permeance of species 'i', $F_i$=Permeate flow rate of species 'i' $\Delta p_i$=transmembrane partial pressure difference of species 'i', and A is the area of the membrane (13.85 cm$^2$), the permeance ($Q_i$) was calculated.

In the Examples, the following abbreviations are used:

HFPO—hexafluoropropylene oxide (For preparation of HFPO dimer peroxide see U.S. Pat. No. 7,112,314, which is hereby included by reference. HFPO dimer [2062-98-8] is available from Synquest Laboratories, Alachua, Fla., USA)

PDD—perfluoro(2,2-dimethyl-1,3-dioxole) or
SEFVE—$CF_2$=$CFOCF_2CF(CF_3)OCF_2CF_2SO_2F$
PPSF—$CF_2$=$CFOCF_2CF_2SO_2F$
VF2—vinylidene fluoride ($H_2C$=$CF_2$)
VF—vinyl fluoride ($H_2C$=CHF)
PPVE—perfluoro(propylvinyl ether)

EXAMPLE 1

Synthesis of PDDNF/SEFVE (Feed Ratio 100:100:150) Copolymer and Hydrolysis

Into a 150 mL stainless steel pressure vessel, after argon purging for 5 minutes, were added a magnetic stirring bar, 3.66 g PDD, 10.04 g SEFVE, 12 mL of Vertrel®XF, (reportedly 1,1,1,2,2,3,4,5,5,5-decafluoropentane and available from The Chemours Co., Wilmington, Del. 19899, USA) 0.6 mL of HFPO dimer peroxide solution (0.12M), and then charged 0.69 g of vinyl fluoride gas at 0° C. The reaction mixture was sealed in the pressure vessel and stirred at room temperature in a water bath. After 3 hours of reaction, the reaction vessel was opened to ambient air, 10 mL acetone and 40 mL methanol was added to the reaction mixture. The resulting gel like precipitate was transferred to a glass dish and dried in oven at 100° C. overnight to yield 5.5 g PDDNF/SEFVE terpolymer as a colorless solid (Tg 37° C.).

Into a 250 mL round bottom flask, were added 3.75 g of the terpolymer synthesized in the previous paragraph, 20 mL deionized water, 60 mL of methanol, 1.85 g ammonium carbonate and a magnetic stirring bar. The reaction mixture was stirred and maintained at 50-60° C. After overnight reaction, a clear solution was obtained. 80 mL 2.0 M hydrochloric acid was added to the mixture and methanol in the mixture was evaporated under heating to form a gel like precipitate. The liquid was decanted and 50 mL of 2.0 M hydrochloric acid was added and stirred for 30 minutes. The liquid was decanted and 80 mL of deionized water was added and then stirred for 30 minutes. After the liquid decanting, the water washing was repeated twice and the solid residue was dried in a vacuum oven at 60° C. for 3 hours. A brownish solid (2.7 g) containing free sulfonic acid groups was obtained.

EXAMPLE 2

Synthesis of PDDNF/PPSF (Feed Ratio 100:100:150) Copolymer and Hydrolysis

Into a 150 mL stainless steel pressure vessel, after argon purging for 5 minutes, were added a magnetic stirring bar, 3.66 g PDD, 6.3 g PPSF, 12 mL of Vertrel®XF, 0.6 mL of HFPO dimer peroxide solution (0.12M), and then charged 0.96 g of vinylidene fluoride gas at 0° C. The reaction mixture was sealed in the pressure vessel and stirred at room temperature in a water bath. After overnight reaction, the reaction vessel was opened to ambient air, 10 mL acetone and 40 mL methanol was added to the reaction mixture. The resulting gel like precipitate was transferred to a glass dish and dried in oven at 100° C. overnight to yield 6.0 g PDDNF/PPSF terpolymer as a colorless solid (Tg 58° C.).

Into a 250 mL round bottom flask, were added 4.0 g of the terpolymer synthesized in the previous paragraph, 20 mL deionized water, 60 mL of methanol, 1.5 g ammonium carbonate and a magnetic stirring bar. The reaction mixture was stirred and maintained at 50-60° C. After overnight reaction, a clear solution was obtained. 80 mL 2.0 M hydrochloric acid was added to the mixture and methanol in the mixture was evaporated under heating to form a gel like precipitate. The liquid was decanted and 50 mL of 2.0 M hydrochloric acid was added and stirred for 30 minutes. The liquid was decanted and 80 mL of deionized water was added and then stirred for 30 minutes. After the liquid decanting, the water washing was repeated twice and the solid residue was dried in a vacuum oven at 60° C. for 3 hours. A slight brownish solid (3.0 g) containing free sulfonic acid groups was obtained.

EXAMPLE 3

Membrane Formation and Testing

Into a glass bottle, were added 0.1 g of the polymer from example 1, 20 mg of silver nitrate, 3.5 g of isopropyl alcohol and 1.5 g of Novec®7300 (reportedly 1,1,1,2,2,3,4,5,5,5-decafluoro-3-methoxy-4-trifluoromethylpentane and available from 3M Corp., Electronic Markets Materials Div., St. Paul, Minn., 55144, USA). The resulting solution was stirred for 1-2 hours, and then filtered through a glass fiber filter having a pore size of 1.2 µm. This solution is denoted as "Solution 1".

Into a glass bottle, were added 0.1 g of the polymer from example 2, 20 mg of silver nitrate, 3.5 g of isopropyl alcohol and 1.5 g of Novec®7300. The resulting solution was stirred for 1-2 hours, and then filtered through a glass fiber filter having a pore size of 1.2 µm. This solution is denoted as "Solution 2".

Into a glass bottle, were added 0.4 g of Aquivion®D79-25BS (obtained from Sigma-Aldrich, USA, and reportedly containing 25 weight percent polymer in water, 1.23-1.30 meq/g of acid capacity on a polymer basis), 20 mg of silver nitrate, 4.6 g of isopropyl alcohol. The resulting solution was stirred for 1-2 hours, and then filtered through a glass fiber filter having a pore size of 1.2 µm. This solution is denoted as "Solution 3".

Into a glass bottle, were added 0.5 g of Nafion®D2020 (obtained from DuPont Fuel Cells, P.O. Box 80701, Wilmington, Del., 19880-0701, USA, and reportedly containing 20 weight percent polymer, about 34 wt % of water, and about 46 wt. % of 1-propanol, 1.03-1.12 meq/g of acid capacity on a polymer basis), 20 mg of silver nitrate, 4.5 g of isopropyl alcohol. The resulting solution was stirred for 1-2 hours, and then filtered through a glass fiber filter having a pore size of 1.2 µm. This solution is denoted as "Solution 4".

A substrate was prepared by coating a 0.2 weight % solution of Teflon® AF2400 (available from the DuPont Co, Wilmington, Del. 19898, USA) (for further information about Teflon® AF, see P. R. Resnick, et al., *Teflon AF Amorphous Fluoropolymers*, J. Schiers, Ed., *Modem Fluoropolymers*, John Wiley & Sons, New York, 1997, p. 397-420, which is hereby included by reference) in Fluorinert® 770 (available from 3M Corp., 3M Center, St. Paul, Minn., USA) on a PAN350 membrane made by Nanostone Water, 10250 Valley View Rd., Eden Prairie, Minn. 53344, USA) (The PAN350 membrane is ultrafilter made from polyacrylonitrile). This substrate is denoted as "Teflon AF/PAN".

Another substrate was prepared by coating 10% Sylgard®184 in n-hexane on PAN350 membrane made. This substrate is denoted as PDMS/PAN.

The Solution 1 was coated on directly PAN350 membrane and coated on Teflon AF/PAN respectively at <30% relative humidity.

The Solution 2 was coated on PAN350 membrane, coated on Teflon AF/PAN and coated on PDMS/PAN respectively at <30% relative humidity.

The Solution 3 was coated on PAN350 membrane, coated on Teflon AF/PAN and coated on PDMS/PAN respectively at <30% relative humidity.

The Solution 4 was coated on PAN350 membrane and coated on Teflon AF/PAN respectively at <30% relative humidity.

Obtained composite membranes are measured the propane and propylene permeances as following method.

The permeance measurement membrane was a 47 mm diameter, a flat sheet. The feed gas composition, 20 mole % propylene (polymer synthesis grade), and 80% propane was humidified by passing it through a water bubbler. The total flow rate of both gases was 200 mL/min. The feed gas (mixture of propylene and propane) was 60 psig, and the sweep gas on the second side of the membrane was humidified nitrogen at a pressure of 0.0 to 0.3 psig. The permeate from the second side of the membrane was analyzed by GC to determine the molar ratio of propane and propylene. Permeances (GPU) are given in $cm^3/cm^2/sec/cm\ Hg \times 10^6$.

Table-1 shows the permeance measurements result:

TABLE 1

| Membrane Material | Permeance (GPU) | | Selectivity |
| --- | --- | --- | --- |
| | $C_3H_8$ | $C_3H_6$ | $C_3H_6/C_3H_8$ |
| Solution 1 on PAN | 2.71 | 78.9 | 29.1 |
| Solution 1 on Teflon AF/PAN | 5.29 | 247.6 | 46.8 |
| Solution 2 on PAN | 2.9 | 79.3 | 27.4 |
| Solution 2 on Teflon ® AF/PAN | 2.9 | 276 | 95.7 |
| Solution 2 on PDMS/PAN | 4.5 | 120.1 | 26.7 |
| Solution 3 on Teflon ® AF/PAN | 5.97 | 311.4 | 52.1 |
| Solution 3 on PAN | 4.45 | 143.7 | 32.3 |
| Solution 3 on PDMS/PAN | 11.1 | 219.7 | 29.2 |
| Solution 4 on PAN | 7.3 | 58.2 | 8.0 |
| Solution 4 on Teflon ® AF/PAN | 5.69 | 212.3 | 37.3 |

It is clear from Table 1 that incorporation of the fluoropolymer HDL in the composite membrane results in a consistent increase in both the propylene permeance and the propylene/propane selectivity.

EXAMPLE 4

Synthesis of a PDD/PPVE High Diffusion Rate Polymer

A glass pressure tube was charged 8.0 g PDD, 872 mg PPVE, 0.8 mL HFPO dimer peroxide solution (0.12 M) in Vertrel XF and 15 mL Vertrel XF. After degassing the mixture for 5 minutes with argon at 0° C., the glass tube was sealed, allowed to warm to room temperature in a water bath and the reaction mixture was stirred overnight. The tube was opened to air and 30 mL acetone is added into the mixture. After stirring for 5 minutes, the mixture was filtered and 30 mL fresh acetone was added to rinse everything out of the vessel. The solid on the filter paper was transferred to a watch glass. After drying in oven at 100° C. overnight, 7.4 g of white solid was collected as the PDD/PPVE polymer.

EXAMPLE 5

Synthesis of a PDD/SEFVE High Diffusion Rate Polymer

A glass pressure tube was charged with 4.88 g PDD, 892 mg SEFVE, 0.4 mL HFPO dimer peroxide solution (0.12 M) in Vertrel XF and 15 mL Vertrel XF. After degassing the mixture for 5 minutes with argon at 0° C., the glass tube was sealed, allowed to warm to room temperature in a water bath and the reaction mixture is stirred overnight. The tube was opened to air and 30 mL acetone was added into the mixture. After stirring for 5 minutes, the mixture was filtered and 30 mL fresh acetone was added to rinse everything out of the vessel. The solid on the filter paper was transferred to a watch glass. After drying in oven at 100° C. overnight, 4.1 g of white solid was collected as the PDD/SEFVE polymer.

EXAMPLE 6

High Diffusion Rate Layer Permeability Measurements

Solutions were prepared from Teflon® AF 2400 in Fluorinert®770 at various concentrations (Table 2) and coated on a PAN350 membrane as described in example 3. It is believed lower polymer concentration results in formation of thinner membranes. These supported membranes were tested for nitrogen permeance at feed pressures of 10, 20 and 30 psig (68.9, 137.8 and 207.7 kPa) and at ambient (atmospheric) pressure on the product side. The results shown in Table 2 for each solution are averages of the three feed pressures.

TABLE 2

| Teflon ® AF 2400 concentration in Fluorinert ®770 (wt %) | Nitrogen Permeance (GPU) |
|---|---|
| 0.3 | 2578 |
| 0.1 | 6184 |
| 0.05 | 12445 |

The invention claimed is:

1. A thin film composite membrane for the separation of alkanes from alkenes, comprising:
    (a) a separation layer comprising a silver ionomer of a polymeric sulfonic acid; and
    (b) a high diffusion rate layer, which is nonporous, of one or more fluorinated polymers having a permeance to nitrogen of at least about 250 GPU, and wherein said separation layer and said high diffusion rate layer are laminated to each other.

2. The thin film composite membrane of claim 1 wherein said silver ionomer is a fluorinated polymer.

3. The thin film composite membrane of claim 1 wherein said silver ionomer is a perfluoropolymer.

4. The thin film composite membrane of claim 1 wherein said high diffusion rate layer is a fluorinated polymer wherein about 50% or more of the total of the carbon fluorine groups and carbon-hydrogen groups are carbon fluorine groups.

5. The thin film composite membrane of claim 1 wherein said high diffusion rate layer fluorinated polymer is a perfluoropolymer.

6. The thin film composite membrane of claim 1 wherein said high diffusion rate layer fluorinated polymer is a perfluorocopolymer of perfluoro(2,2-trifluoromethyl-1,3-dioxole).

7. The thin film composite membrane of claim 1 wherein said high diffusion rate layer fluorinated polymer is a copolymer of perfluoro(2,2-trifluoromethyl-1,3-dioxole) and tetrafluoroethylene.

8. The thin film composite membrane of claim 1 wherein said high diffusion rate layer is about 0.1 to about 1.0 μm thick.

9. The thin film composite membrane of claim 1 additionally comprising a porous layer which is laminated to said high diffusion rate layer.

10. The thin film composite membrane of claim 4 additionally comprising a porous layer which is laminated to said high diffusion rate layer.

11. The thin film composite membrane of claim 5 additionally comprising a porous layer which is laminated to said high diffusion rate layer.

12. The thin film composite membrane of claim 6 additionally comprising a porous layer which is laminated to said high diffusion rate layer.

13. The thin film composite membrane of claim 7 additionally comprising a porous layer which is laminated to said high diffusion rate layer.

14. The thin film composite membrane of claim 13 wherein said high diffusion rate layer is about 0.1 to about 1.0 μm thick.

15. A membrane process for the separation of alkanes from alkenes, wherein the improvement comprises, using a thin film composite membrane, comprising:
    (a) a separation layer comprising a silver ionomer of a polymeric sulfonic acid; and
    (b) a high diffusion rate layer, which is nonporous, of one or more fluorinated polymers having a permeance to nitrogen of at least about 250 GPU, and wherein said separation layer and said high diffusion rate layer are laminated to each other.

16. The membrane process of claim 15 wherein said silver ionomer is a fluorinated polymer.

17. The membrane process of claim 15 wherein said silver ionomer is a perfluoropolymer.

18. The membrane process of claim 15 additionally comprising a porous layer which is laminated to said high diffusion rate layer.

19. The membrane process of claim 15 wherein said high diffusion rate layer is a fluorinated polymer wherein about 50% or more of the total of the carbon fluorine groups and carbon-hydrogen groups are carbon fluorine groups.

20. The membrane process of claim 15 wherein said high diffusion rate layer fluorinated polymer is a perfluoropolymer.

21. The membrane process of claim 15 wherein said high diffusion rate layer fluorinated polymer is a perfluorocopolymer of perfluoro(2,2-trifluoromethyl-1,3-dioxole).

22. The membrane process of claim 21 wherein said high diffusion rate layer fluorinated polymer is a copolymer of perfluoro(2,2-trifluoromethyl-1,3-dioxole), and tetrafluoroethylene.

23. The membrane process of claim 15 wherein said high diffusion rate layer is about 0.1 to about 1.0 μm thick.

24. The membrane process of claim 21 wherein said high diffusion rate layer is about 0.1 to about 1.0 μm thick.

25. The thin film composite membrane of claim 2 wherein said high diffusion rate layer is a fluorinated polymer wherein about 50% or more of the total of the carbon fluorine groups and carbon-hydrogen groups are carbon fluorine groups.

26. The thin film composite membrane of claim 3 wherein said high diffusion rate layer is a fluorinated polymer wherein about 50% or more of the total of the carbon fluorine groups and carbon-hydrogen groups are carbon fluorine groups.

27. The thin film composite membrane of claim 2 wherein said high diffusion rate layer fluorinated polymer is a perfluoropolymer.

28. The thin film composite membrane of claim 3 wherein said high diffusion rate layer fluorinated polymer is a perfluoropolymer.

29. The thin film composite membrane of claim 2 wherein said high diffusion rate layer fluorinated polymer is a perfluorocopolymer of perfluoro(2,2-trifluoromethyl-1,3-dioxole).

30. The thin film composite membrane of claim 3 wherein said high diffusion rate layer fluorinated polymer is a perfluorocopolymer of perfluoro(2,2-trifluoromethyl-1,3-dioxole).

31. The thin film composite membrane of claim 2 wherein said high diffusion rate layer fluorinated polymer is a copolymer of perfluoro(2,2-trifluoromethyl-1,3-dioxole) and tetrafluoroethylene.

32. The thin film composite membrane of claim 3 wherein said high diffusion rate layer fluorinated polymer is a copolymer of perfluoro(2,2-trifluoromethyl-1,3-dioxole) and tetrafluoroethylene.

33. The thin film composite membrane of claim 2 wherein said high diffusion rate layer is about 0.1 to about 1.0 µm thick.

34. The thin film composite membrane of claim 3 wherein said high diffusion rate layer is about 0.1 to about 1.0 µm thick.

35. The thin film composite membrane of claim 2 additionally comprising a porous layer which is laminated to said high diffusion rate layer.

36. The thin film composite membrane of claim 3 additionally comprising a porous layer which is laminated to said high diffusion rate layer.

37. The membrane process of claim 16 additionally comprising a porous layer which is laminated to said high diffusion rate layer.

38. The membrane process of claim 17 additionally comprising a porous layer which is laminated to said high diffusion rate layer.

39. The membrane process of claim 16 wherein said high diffusion rate layer is a fluorinated polymer wherein about 50% or more of the total of the carbon fluorine groups and carbon-hydrogen groups are carbon fluorine groups.

40. The membrane process of claim 17 wherein said high diffusion rate layer is a fluorinated polymer wherein about 50% or more of the total of the carbon fluorine groups and carbon-hydrogen groups are carbon fluorine groups.

41. The membrane process of claim 18 wherein said high diffusion rate layer is a fluorinated polymer wherein about 50% or more of the total of the carbon fluorine groups and carbon-hydrogen groups are carbon fluorine groups.

42. The membrane process of claim 16 wherein said high diffusion rate layer fluorinated polymer is a perfluoropolymer.

43. The membrane process of claim 17 wherein said high diffusion rate layer fluorinated polymer is a perfluoropolymer.

44. The membrane process of claim 18 wherein said high diffusion rate layer fluorinated polymer is a perfluoropolymer.

45. The membrane process of claim 16 wherein said high diffusion rate layer fluorinated polymer is a perfluorocopolymer of perfluoro(2,2-trifluoromethyl-1,3-dioxole).

46. The membrane process of claim 17 wherein said high diffusion rate layer fluorinated polymer is a perfluorocopolymer of perfluoro(2,2-trifluoromethyl-1,3-dioxole).

47. The membrane process of claim 18 wherein said high diffusion rate layer fluorinated polymer is a perfluorocopolymer of perfluoro(2,2-trifluoromethyl-1,3-dioxole).

48. The membrane process of claim 16 wherein said high diffusion rate layer is about 0.1 to about 1.0 µm thick.

49. The membrane process of claim 17 wherein said high diffusion rate layer is about 0.1 to about 1.0 µm thick.

50. The membrane process of claim 18 wherein said high diffusion rate layer is about 0.1 to about 1.0 µm thick.

\* \* \* \* \*